United States Patent [19]

Kalakutsky et al.

[11] Patent Number: 4,556,849

[45] Date of Patent: Dec. 3, 1985

[54] APPARATUS FOR MEASURING THE GRAIN-SIZE COMPOSITION OF POWDERS

[75] Inventors: Lev I. Kalakutsky, Kuibyshev; Vladimir V. Sychenkov; Vladimir B. Vlasov, both of Tolyatti, all of U.S.S.R.; Adolf V. Dubrovsky, deceased, late of Tolyatti, U.S.S.R., by Nina V. Dubrovskaya, administrator

[73] Assignee: Vsesojuzny Nauchno-Issledovatelsky Institut Nerudnykh Stroitelnykh Materialov Gidromekhanizatsii, Tolyatti, U.S.S.R.

[21] Appl. No.: 470,956

[22] Filed: Mar. 1, 1983

[51] Int. Cl.$^4$ .............................................. G01N 27/62
[52] U.S. Cl. ...................................... 324/464; 324/455
[58] Field of Search ..................... 324/464, 459, 455; 335/154, 151, 152, 153

[56] References Cited

U.S. PATENT DOCUMENTS 3,718,029 2/1973 Gourdine et al. ........................ 73/28
3,763,449 10/1973 Kimball .............................. 335/151
4,286,241 8/1981 Olivenbaum et al. .............. 335/154

FOREIGN PATENT DOCUMENTS 372483 5/1973 U.S.S.R. .
530229 2/1977 U.S.S.R. .

Primary Examiner—Ernest F. Karlsen
Assistant Examiner—Kevin D. O'Shea
Attorney, Agent, or Firm—Fleit, Jacobson, Cohn & Price

[57] ABSTRACT

An improved apparatus for measuring the grain-size composition of powders in which a device for transforming a powder into a gaseous flow of individual particles, a charging chamber in which each particle acquires a charge which is proportional to its surface area, a precipitating capacitor in which the flow of charged particles is separated into various fractions in accordance with the charge on the particles, an electrometric device for measuring the total charge of individual fractions are provided, the electrometric device having inductive sensors of charged particles, the number of inductive sensors being equal to the number of fractions, and an amplifier to which are connected all inductive sensors of charged particles. The improvement comprises a plurality of switching devices, one switching device being provided for each sensor. Each switching device has an input and an output, includes a sealed contact means for avoiding charge leakage from the respective sensors, and is positioned between an inductive sensor and the amplifier.

6 Claims, 2 Drawing Figures

U.S. Patent   Dec. 3, 1985   4,556,849

APPARATUS FOR MEASURING THE GRAIN-SIZE COMPOSITION OF POWDERS

FIELD OF THE ART

The invention relates to the equipment for the analysis of pulverulent materials, and more specifically it deals with apparatus for measuring the grain-size composition of powders.

The invention may be used for the analysis of grain-composition of microscopic powders within the grain-size range from 63 to 0.5 μm, e.g. in the medical, perfumery and chemical industries as well as in the manufacture and applications of such materials as talc, kaolin, chalk, quartz, mica, porcelain, cement and abrasive materials.

BACKGROUND OF THE INVENTION

Known in the art are apparatus for studying physical properties of industrial aerosols and pulverulent materials functioning on the basis of preliminarily charging particles, with subsequent handling of electrical signals obtained in measuring charges of the particles (cf. USSR Inventor's Certificate No. 372483, Cl. G 01 N 15/02, 1973; U.S. Pat. No. 3,718,029, Cl. 73-28, 1973).

Such apparatus comprises a gas duct for forming a flow of suspended particles, a charging device in the form of an electrode generating a corona discharge wherein particles acquire a charge which is proportional to their surface area, and a device for measuring the total charge of the particles.

The disadvantage of such apparatus resides in that it can mainly measure the concentration of particles of industrial aerosols or pulverulent materials per unit of volume. The application of such apparatus for the analysis of grain-size composition is rather difficult.

In addition, the analysis of grain-size composition of a powder in prior art apparatus is performed during a time period between several hours and several days which makes the production process requiring such an analysis very complicated.

Known in the art is an apparatus for measuring the grain-size composition of powders, comprising a device for transforming a powder into a gaseous flow of individual particles (a powder sample atomizer), an inlet pipe connected thereto and having a narrow tube for forming a jet of aerosol, and a filter for cleaning the gas and for laminarizing the flow.

The apparatus also comprises a charging chamber communicating with the inlet pipe, a precipitating capacitor in the form of a U-shaped pipe, and a device for measuring the total charge of individual fractions. This device has inductive sensors of charged particles, the number of the sensors being equal to the number of fractions, each sensor being installed in a collector plate of the precipitating capacitor, and an electrometric amplifier having an input to which are connected said inductive sensors. A pulse train characterizing the grain-size composition of the powder under study appears at the output of the amplifier (cf. USSR Inventor's Certificate No. 530229, Cl, G 01 N 15/00, 1977). The prior art apparatus also has an air blower, a device for neutralizing static charges and high-voltage power supply sources connected to the charging chamber and precipitating capacitor.

A sample of the powder under study is transformed into a gas flow of individual particles and is admitted to the charging chamber through a narrow tube of an inlet pipe in the form of an aerosol jet. In the charging chamber with an unipolar space charge the particles are charged, the particles of the same size acquiring equal charges. The flow of charged particles is then fed to the precipitating capacitor in which the dispersed phase of the aerosol is distributed in the space into fractions under the action of forces of the electrostatic field, the fractions precipitating at different distances from the point of entry of the flow to the precipitating capacitor. The sensors generate signals, each signal corresponding to the value of charge of particles of a given fraction so as to characterize the size of the particles. The signals are fed to the electrometric amplifier having an output at which a pulse train appears which characterizes the grain-size composition of the powder under study. After the signal is recorded, dust is removed and static charges are neutralized.

The disadvantage of this apparatus resides in that the direct connection of the inductive sensors to the electrometric amplifier results in a substantial leakage of charge containing information on a given fraction which is obtained from the inductive sensor.

This is explained by the fact that the basic condition according to which the time t of measurement of the grain-size composition should be much shorter than the time constant $\tau$ of the inductive sensor during which the value of the total charge of the particles remains unchanged, that is $t<<\tau$, is not fulfilled. As the time constant of the inductive sensor is determined by the formula $\tau=RC$, wherein R is the input resistance of the amplifier and C is the capacitance of the sensor, it is obvious that the required value of the time constant $\tau$ of the inductive sensor can only be obtained by making a compromise between the two parameters R and C.

Generally for a majority of apparatus of this type the time t of measurement of the grain-size composition is longer than 100 s. At the same time, the value of the sensor capacitance is determined by the relationship $U=Q/C$, wherein Q is the total charge of particles of a given fraction, and to achieve the required voltage level U obtained at the sensor, the value of the sensor capacity C should be maximum 100 pF.

Therefore, in order to comply with the requirement that $t<<\tau$, it is necessary that the input resistance of the amplifier R should be greater than $10^{13}\Omega$. In the case where the induction sensor is directly connected to the electrometric amplifier, it is not possible to have such an input resistance R as the existing amplifiers have the resistance of maximum $10^9\Omega$ at the input, and the condition $t<<\tau$ is not fulfilled. This results in a substantial error in the measurement of the grain-size composition.

SUMMARY OF THE INVENTION

It is an object of the invention to provide an apparatus for measuring grain-size composition of a powder which can ensure the accuracy of the analysis of the grain-size composition of a powder which is substantially better than the accuracy obtainable in prior art apparatus.

Another object of the invention is to substantially accelerate the analysis.

This is accomplished by that in an apparatus for measuring the grain-size composition of powders, comprising a device for transforming a powder into a gaseous flow of individual particles, a charging chamber communicating therewith in which each particle acquires a charge which is proportional to its surface area, a precipitating capacitor to which the flow of the charged particles is fed to be separated therein into various fractions in accordance with the particle size, a device for measuring the total charge of individual fractions having sensors of charged particles, the number of the sensors being equal to the number of fractions, each sensor being installed in a collector plate of the precipitating capacitor and connected to an electrometric amplifier having an output at which a pulse train appears which characterizes the grain-size composition of the powder under study, according to the invention, the device for measuring the total charge of individual fractions has switching devices each comprising a sealed contact and each having an input connected to the output of a respective sensor of charged particles, the sensor being connected to the input of the electrometric amplifier through the switching device.

Each sealed contact is preferably insulated from external factors, and for that purpose it is installed coaxially with and inside a metal sleeve on which is installed a winding for actuating the sealed contact, the leads of the sealed contact being secured coaxially in two insulating washers, each washer being installed at one end of the metal sleeve.

The insulating washer may be intalled in grooves of flanges provided on the metal sleeve, and the sealed connection of the insulating washers is ensured by means of projections provided in the grooves of the flanges, the insulating washers being sealingly urged against the projections by means of nuts.

BRIEF DESCRIPTION OF THE DRAWINGS

Other objects and advantages of the invention will become apparent from the following description of specific embodiments thereof illustrated in the accompanying drawings, in which.

DETAILED DESCRIPTION OF THE INVENTION

An apparatus for measuring the grain-size composition of powders comprises a device 1 (FIG. 1) for transforming a powder into a gaseous flow of individual particles, a charging chamber 2 communicating therewith in which each particle of the powder acquires a charge which is proportional to its surface area. The charging chamber 2 is of a conventional design and comprises, e.g. two corona discharge compartments and one charging compartment. Provided adjacent to the charging chamber 2 is an electrostatic precipitator 3 for cleaning air and for laminarizing the air flow, the precipitator communicating with a precipitating capacitor 4 to which the flow of charged particles is fed.

Figure 1:
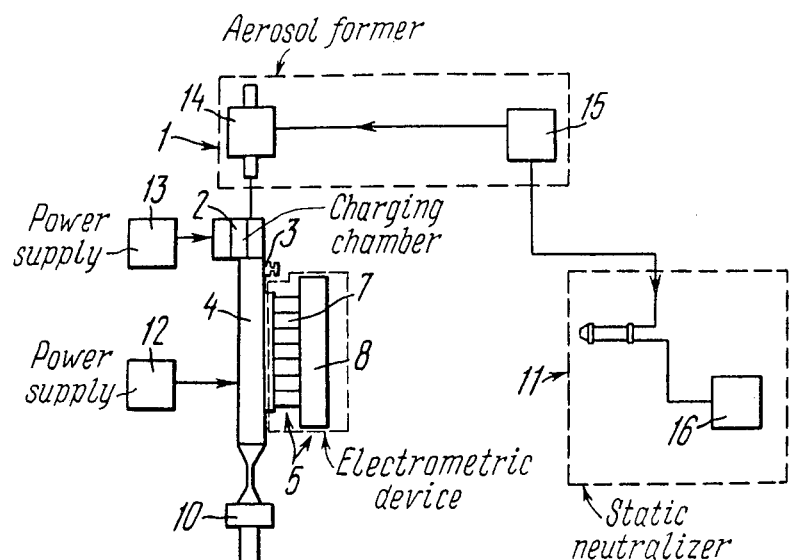
FIG. 1 is a structural diagram of an apparatus for measuring the grain-size composition according to the invention.

The apparatus also comprises a device 5 for measuring the total charge of individual fractions, i.e., an electrometric device which has inductive sensors 6 (FIG. 2) of charged particles, switching devices 7 (FIG. 1) and an electrometric amplifier 8. The number of the sensors 6 (FIG. 2) is equal to the number of fractions into which the flow of charged particles is divided, and each sensor 6 is installed in a collector plate 9 (FIG. 2) of the precipitating capacitor 4 (FIG. 1). An output of each sensor 6 is connected to one lead of a respective switching device 7 having the other lead which is connected to an input of the electrometric amplifier 8. Thus each sensor 6 of charged particles is connected to the input of the electrometric amplifier 8 through a respective switching device 7.

The apparatus also comprises an air blower 10 providing for the passage of the flow of individual particles of the powder through the charging chamber 2, precipitator 3 and precipitating capacitor 4; a device 11 for neutralizing static charges in the precipitating capacitor 4; and high-voltage power supply sources 12, 13 for supplying the charging chamber 2 and the precipitating capacitor 4, respectively.

The device 1 for transforming the powder into a gaseous flow of individual particles comprises a powder atomizer 14 and air blower 15, a device for supplying air which also supplies air to the device 11 for neutralizing static charges.

FIG. 1 also shows a power supply unit 16 of the device 11.

Figure 2:
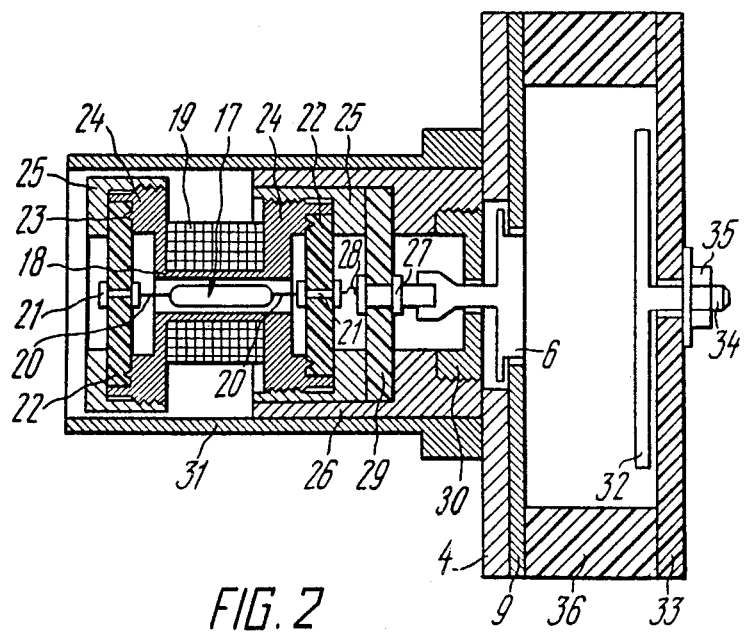
FIG. 2 shows one of switching devices according to the invention.

FIG. 2 shows the switching device comprising a sealed contact 17 which is installed coaxially with and inside a metal sleeve 18 to avoid the influence of external electrical and environmental factors. A winding 19 for actuating the sealed contact 17 is installed on the sleeve 18 and has leads 20 which are coaxially installed in electrically insulating washers 22 by means of bushings 21.

The washers 22 are placed at the ends of the metal sleeve 18. The insulating washers 22 are sealingly connected to the metal sleeve 18 by means of projections 23 provided in grooves of flanges 24 of the metal sleeve 18, the insulating washers 22 being sealingly urged against the projections by means of nuts 25. The switching device 7 and the inductive sensors 6 are coaxially installed in a sleeve 26, and the electric contact therebetween is effected by means of a metal rod 27 and a connector 28. The rod 27 and the connector 28 are fixed at the center of an insulating washer 29 which is coaxially installed in the sleeve 26 between the switching device 7 and the inductive sensor 6.

An end wall, i.e., surface, of the sleeve 26 comprises a threaded lid 30 which makes it possible to adjust the capacitance between the interior of the inductive sensor 6 and the end wall of the sleeve 26. The sleeve 26 is secured to the collector plate 9 of the precipitating capacitor 4 by means of a hollow cylinder 31.

Apart from the collector plate 9, the precipitating capacitor 4 has a high-voltage electrode 32 which is rigidly secured to an insulating plate 33 by means of a screw 34 and a nut 35. The collector plate 9 is parallel to and spaced apart from the high-voltage electrode 32 for providing a path for the flow of charged particles. The charged particles precipitate onto the plate 9, and this plate is separated from the high-voltage electrode 32 by insulating plates 36.

The apparatus functions in the following manner.

A sample of the powder being analyzed is fed into the atomizer 14 and is transformed, by means of the air blower 15, into a gaseous flow of particles admitted to the charging chamber 2.

A corona discharge occurs in the charging chamber, which is formed by the power supply source 13, whereby the particles acquire unipolar high-voltage charges which are proportional to the surface area of the particles (in particular, to the second power of their diameter). At the same time, the flow jet diverges. The flow of charged particles is fed by the air blower 10 from the charging chamber to the precipitating capacitor 4 having at the inlet thereof the electrostatic precipitator 3 for fixing the point of entry of the charged particles to the precipitating capacitor 4.

Under the action of forces of the electrostatic field formed by the power supply source 12, the particles are distributed over the space within the precipitating capacitor and separated into fractions, and these fractions precipitate within various zones of the collector plate 9 having, at the center thereof, the inductive sensors 6 one for each fraction.

During the time the precipitation occurs and the charges are accumulated at the inductive sensors 6, the sensors are disconnected from the electrometric amplifier 8. The total accumulated charge Q contains information on the quantity of particles of a given fraction, since $Q=n\cdot q$, wherein n is the quantity of particles in the fraction and q is the charge of a single particle.

The value of the accumulated charge after the precipitation of a given fraction remains unchanged during the entire process of measurement. After the flow is divided into fractions, the inductive sensors 6 are alternately connected to the input of the electrometric amplifier 8 through the switching devices 7, and the accumulated charge flows from the induction sensor 6 through the input resistance of the amplifier 8 so that a voltage pulse appears at the output of the amplifier 8 with an amplitude which exactly corresponds to the quantity of particles contained in a given fraction.

Charge leakage from the sensors 6 is avoided by that the insulating washers 22 are sealingly urged against the flanges 24 of the metal sleeve 18 by means of the nuts 25 and conical projections 23 at the point where the washer 22 engages the flange of the sleeve 18.

After the measurement, static charges are neutralized by the device 11 which is supplied by the air blower 15 and power supply source 16.

The use of the switching device which is insulated from the influence of external factors makes it possible to substantially improve the accuracy of measurement and reliability of the apparatus, enlarge the range of charges being measured, reduce the time required for the analysis of the grain-size composition of powders and also to provide apparatus for the analysis of the grain-size composition of powders which can operate not only under laboratory conditions but also in the field.

We claim:

1. In an apparatus for measuring grain-size composition of powders, including:
   a device for transforming a powder into a gaseous flow of individual particles;
   a charging chamber communicating with said device for transforming the powder, each particle of the powder acquiring a charge proportional to its surface area in said charging chamber;
   a precipitating capacitor having a high-voltage electrode and a collector plate which are placed parallel to one another and spaced apart so as to define there between a path for the passage of the flow of charged particles from said charging chamber, the flow of charged particles being separated in said precipitating capacitor into various fractions in accordance with the charge on the particles; and
   an electrometric device for measuring the total charge of individual fractions are provided, said electrometric device, comprising a plurality of inductive sensors of charged particles, the number of the inductive sensors being equal to the number of fractions, each said inductive sensor having an input and an output, and being installed in the collector plate of the precipitating capacitor, a signal being formed during operation of the apparatus at the output of the inductive sensor of charged particles which is proportional to the total charge of all particles of a given fraction; and an amplifier having an input and an output, wherein the improvement comprises:
   a plurality of switching devices, one switching device being provided for each sensor, each switching device having an input and an output and including a sealed contact means for avoiding charge leakage from the respective sensors; the input of each switching device being connected to the output of the respective sensor; the output of each switching device being connected to the input of the amplifier; a pulse train appearing at the output of the amplifier during operation of the apparatus which characterizes the grain-size composition of the powder being studied.

2. An improved apparatus according to claim 1, wherein each sealed contact means comprises a sealed contact which is insulated from the influence of external electrical and environmental factors.

3. An improved apparatus according to claim 2, wherein, for insulating from the influence of external electrical and environmental factors, each switching device further comprises:
   a metal sleeve within which the sealed contact is coaxially positioned;
   a winding for actuating the sealed contact which is installed on the metal sleeve;
   two leads for said sealed contact, the leads connected one at each end of the sealed contact;
   two electrically insulating washers sealingly installed one at each end of the metal sleeve;
   said two leads of the sealed contact being secured coaxially in and through one of the electrically insulating washers.

4. An improved apparatus according to claim 3, wherein each switching device further comprises:
   flanges provided one at each end of said metal sleeve;
   a groove provided in each flange, each electrically insulating washer being adapted for installation in said groove; and
   a projection provided in each groove, each electrically insulating washer being sealingly urged against said projection.

5. An improved apparatus according to claim 4, wherein each switching device further comprises means for adjusting the capacitance between each sensor and each respective switching device.

6. An improved apparatus according to claim 5, wherein each switching device further comprises a hollow cylindrical housing positioned coaxially around the sealed contact, the metal sleeve, the flanges, the winding, and the two electrically insulating washers, and a threaded lid positioned on a first end of the hollow cylinder, said first end of the hollow cylinder having a threaded sleeve positioned along the inner surface thereof which threadingly engages the threaded lid to thereby provide said means for adjusting the capacitance between each sensor and each respective switching device, the first end of the hollow cylindrical housing and an end surface of the threaded sleeve abutting the collector plate of the precipitating capacitor along the surface thereof remote from the path for the passage of flow of charged particles and coaxially surrounding the sensor installed in the collector plate such that an adjustment in the threaded engagement between the threaded lid and the threaded sleeve changes the spacing between the surface of the sensor which faces the threaded lid and the end surface of the threaded sleeve.

* * * * *